United States Patent [19]

Keyes et al.

[11] Patent Number: 4,482,918
[45] Date of Patent: Nov. 13, 1984

[54] METHOD AND APPARATUS FOR X-RAY IMAGE SUBTRACTION

[75] Inventors: Gary S. Keyes, Hartland; Stephen J. Riederer, Wauwatosa; Thomas W. Lambert, Dousman; Barry N. Stone, Waukesha, all of

[73] Assignee: General Electric Company, Schenectady, N.Y.

[21] Appl. No.: 371,683

[22] Filed: Apr. 26, 1982

[51] Int. Cl.³ .............................................. H04N 5/32
[52] U.S. Cl. ........................................ 358/111; 378/99
[58] Field of Search .................... 358/111; 378/99, 100

[56] References Cited

U.S. PATENT DOCUMENTS

| | | | |
|---|---|---|---|
| 3,974,386 | 8/1976 | Mistretta | 250/402 |
| 4,204,225 | 5/1980 | Mistretta | 358/111 |
| 4,204,226 | 5/1980 | Mistretta | 358/111 |
| 4,335,307 | 6/1982 | De Vries et al. | 358/111 |
| 4,355,331 | 10/1982 | Georges et al. | 358/111 |

Primary Examiner—Joseph A. Orsino, Jr.
Attorney, Agent, or Firm—Fuller, House & Hohenfeldt, S.C.

[57] ABSTRACT

Apparatus and methods are provided for performing temporal and hybrid subtraction of X-ray images. In one mode, using three memories, a pair of low and high energy X-ray exposures are made before an X-ray contrast medium arrives in a blood vessel to provide mask images. After contrast arrival additional high and low energy exposures are made and the low energy mask is subtracted from the low energy post-contrast images and the high energy mask is subtracted from the high energy post-contrast images and the resulting sequence of low and high energy temporal difference images are stored. The low energy temporal difference images are displayed. If motion artifacts are perceived, hybrid subtraction of low and high energy temporal difference images is undertaken to produce an image data set in which motion artifacts are removed. In an alternate mode, which uses four memories, low and high energy pre-contrast mask images are stored in one pair of memories. Low and high energy live post-contrast images are subtracted from the stored images and the resulting low and high energy temporal difference images are stored in the other pair of memories. These are subtracted to produce hybrid images.

16 Claims, 8 Drawing Figures

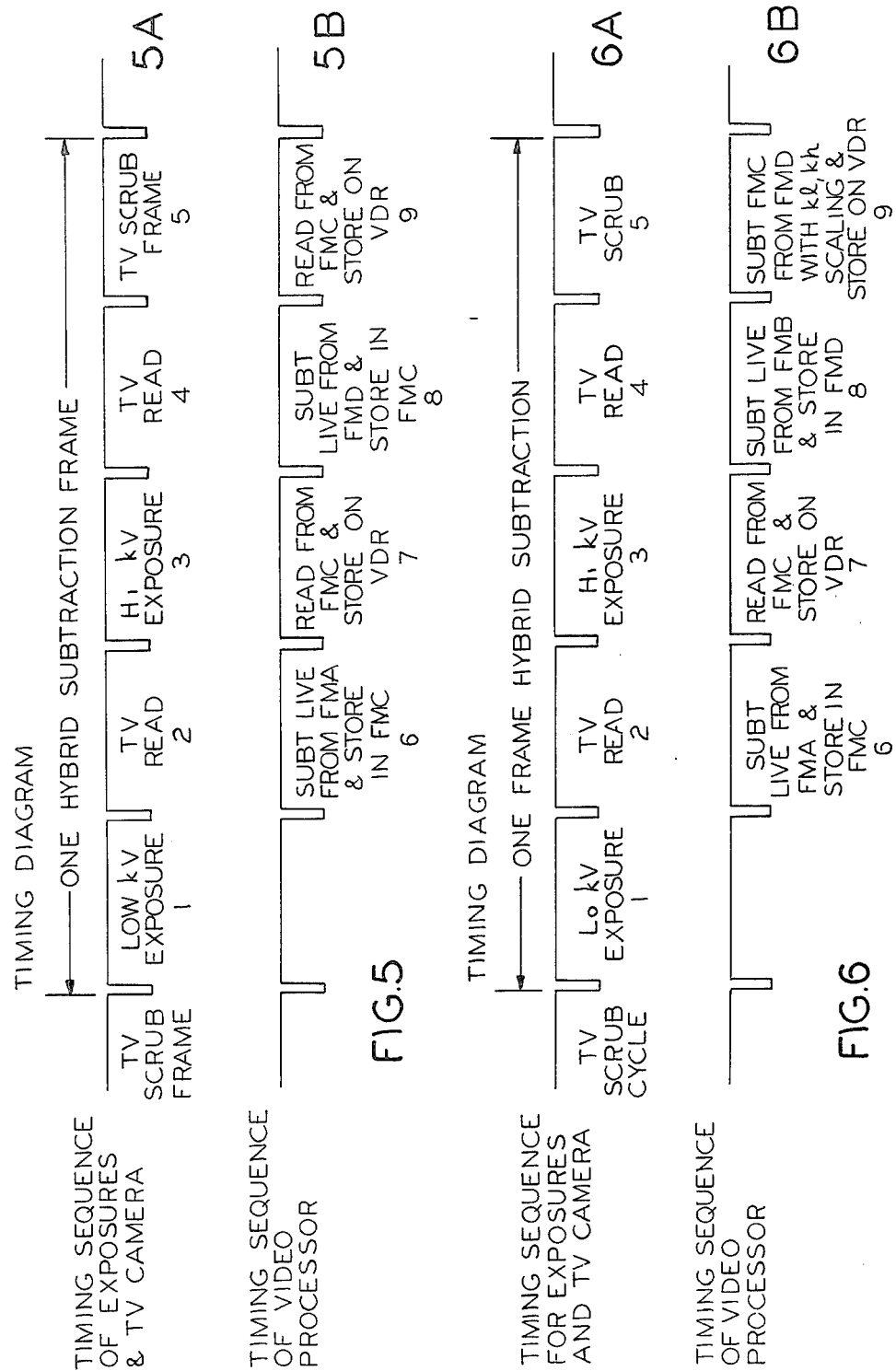

METHOD AND APPARATUS FOR X-RAY IMAGE SUBTRACTION

BACKGROUND OF THE INVENTION

This invention pertains to X-ray image subtraction methods and to apparatus for performing such methods.

Digital X-ray image subtraction systems are now being used to visualize the blood vessels in the body. The subtraction procedure involves making an X-ray image, called a mask image, of a region of interest in the body. The mask image is digitized and the digital data representative of picture elements in the mask image are placed in a digital frame memory. At some time, usually just before the mask image is obtained, an X-ray contrast medium such as an iodinated compound is injected intravenously. When the contrast medium reaches the vessels in the region of interest, a series of X-ray images are made and they are converted to digital data. The mask or pre-contrast image data are then subtracted from the post-contrast image data to cancel or subtract out all soft tissue and bone structure common to both images to thereby enhance visualization of the blood vessels that contain the contrast medium. The method is commonly called temporal subtraction imaging because of the substantial time lapse between the pre-contrast and post-contrast images. One type of apparatus for performing temporal subtraction methods is described in U.S. Pat. No. 4,204,225.

One of the problems with temporal subtraction techniques is that there may be a substantial loss of registration between the mask and post-contrast images due, primarily, to movement of soft tissue. Movement of soft tissue or anything else between the two stored images will result in blurring or artifacts in the subtracted or difference image and will distort or obliterate the desired image of the blood vessels containing the contrast medium.

With temporal subtraction it is often possible to achieve good cancellation or subtraction of bone, which usually does not move involuntarily, but some atifacts or misregistrations may result from involuntary tissue motion such as that due to swallowing, breathing, peristalsis and blood vessel expansion and contraction.

Another image subtraction technique is characterized as energy subtraction. Energy subtraction is based on the fact that X-ray attenuation by a body or any material is an X-ray energy dependent phenomenon and that the energy dependence is different for materials having different atomic number averages. In the energy subtraction technique, an X-ray image of a region of interest in the body is obtained with a nominally low kilovoltage (kV) applied to the X-ray tube so the beam projected through the body has an energy spectral distribution within a band having low average energy. In digital fluorography, an X-ray image intensifier tube is used to obtain the image and it is viewed with a video camera whose signals are digitized and stored as an image frame. After the relatively low energy image is obtained, another image is obtained with a comparatively higher kV applied to the X-ray tube and a resulting higher average energy spectral band. For ordinary tissue studies the two images may be made in the absence of any contrast medium. For arteriographic studies, the two images are obtained when there is an X-ray contrast medium such as an iodinated compound present in the blood vessels.

In any case, the high average energy image picture element (pixel) data are subtracted from the low average image data and a difference image remains. Prior to subtraction, the data are usually variously weighted or scaled to bring about cancellation of soft tissue. The data could be scaled to reduce bone, too. However, it is not possible to remove or cancel bony structures without also removing most of the iodinated contrast medium which is really what one is trying to visualize in arteriographic studies.

There are also brightness non-uniformities in the subtracted or difference image due to several effects when the data are acquired using an image intensifier. Veiling glare, which is like haze, results from light diffusing or feeding back from areas of the input fluorescent screen of the intensifier to other areas. The fact that rays of a broad X-ray beam are scattered by body tissue in an energy dependent manner between ray paths also causes loss of image contrast. Differential detection of X-rays at various energies in the input phosphor of the image intensifier leads to additional brightness non-uniformities. None of these phenomena can be completely nullified by energy subtraction alone.

An improved hybrid subtraction method, using low and high average X-ray energy spectral bands to make exposures, has been proposed by W. R. Brody in pending patent application Ser. No. 260,694, filed May 5, 1981 now U.S. Pat No. 4,445,226. The hybrid subtraction method uses a combination of energy and temporal subtraction techniques. In hybrid subtraction, X-ray images are obtained at two different average X-ray energies, that is, with two different kilovoltages applied to the tube and the images are combined in a manner to suppress signals due to soft tissue in a heterogeneous object such as the body.

At this juncture it should be noted that the X-ray beams having low and high average energies or energy spectral bands can be obtained in various ways. One way is by applying a constant kilovoltage (kV) to the X-ray tube and interposing two different filters alternatingly in the beam. One filter is for softening the X-ray beam, that is, for removing high energy spectra above a low energy average energy band. Typically, a desired low energy spectral band is determined and a filter is chosen that has relatively low attenuation at X-ray energies below its k-edge and has high attenuation for energies above the k-edge to thereby remove such high energy spectra. A filter made of a rare earth element such as cerium or erbium are examples. The other filter is for hardening the high energy beam and would be composed of a material that attenuates or absorbs the low energy band intensely. Thus, the high energy spectra filter can be aluminum, copper or brass, as examples.

Another way to generate low and high average energy X-ray beams is to switch the X-ray tube applied voltages between low and high levels. Still another way is to switch the X-ray tube applied voltage and switch filters correspondingly. This is the preferred way.

In hybrid subtraction a mask image is obtained first by projecting a low average energy X-ray beam (hereafter called low energy beam or low energy spectral band) through the body followed by a higher average energy X-ray beam (hereafter called high energy beam or high energy spectral band) when the intravenously injected X-ray contrast medium has not yet entered the blood vessels in the anatomical region of interest. The images, consisting primarily of bone and soft tissue acquired at the two energies, are scaled or weighted, using appropriate constants, and then subtracted to produce a mask image in which signals due to soft tissue variations are suppressed and bony structures remain. The data for a pair of high and low energy X-ray images are next obtained when the intravenously injected iodinated compound or other X-ray contrast medium reaches the vessels in the region of interest. The data for this pair of images are acted upon by the same constant weighting factors that were used with the first pair of images and one image in this pair is subtracted from the other such that the resulting post-contrast image contains data representative of bone structures plus vessels containing contrast medium. The final step in hybrid subtraction is to subtract the dual energy post-contrast image from the dual energy pre-contrast mask image to thereby suppress or cancel the bone structures and isolate the contrast medium containing vessels. A major advantage of the hybrid subtraction technique over temporal subtraction alone is the reduced sensitivity to soft tissue motion artifacts because the soft tissue is suppressed or cancelled in both dual energy images.

Hybrid subtraction is a good technique for eliminating anything that may have moved during the time between obtaining the mask image and post-contrast image or images. However, if there is no movement during ordinary temporal subtraction, wherein the post-contrast image is simply subtracted from the pre-contrast mask image, then temporal subtraction images can be used because they generally have a better signal-to-noise ratio (SNR) than hybrid subtraction images. A higher SNR results in displayed images that have better contrast at a given noise level.

Scattering of the X-ray beam by the body is also considered. Scatter in an image depends on X-ray beam energy, beam path length and density of the object being penetrated. In the hybrid subtraction technique the scattering that results from use of a broad cross section X-ray beam is of little consequence since scatter is essentially the same for each energy subtracted pair of images. Hence, scatter effects on image brightness nonuniformities are subtracted out when the pairs are subtracted.

To recapitulate, hybrid digital fluorography techniques provide the merits of soft tissue motion insensitivity, effective bone cancellation, and elimination, to the first order, of scatter and other nonlinear effects in the X-ray image intensifier and the video camera.

SUMMARY OF THE INVENTION

A primary object of the invention is to provide apparatus for simultaneously performing both hybrid digital subtraction methods and temporal digital subtraction methods rapidly and accurately.

Another object is to provide for optionally displaying a subtraction image based on temporal subtraction or hybrid subtraction. In other words, the new apparatus and method is such that the user can display the temporally obtained subtraction image and if it appears that the image quality is reduced because of motion or other artifacts, then the hybrid subtracted images can be retrieved and displayed.

In accordance with one embodiment of the invention, the low energy pre-contrast image data and the low X-ray energy post-contrast image data are stored in a memory or on a magnetic storage medium such that these data can be subtracted to provide a temporal subtracted image having a high signal-to-noise ratio. The hybrid difference images are produced after acquisition of images at the user's option in a reprocessing mode using the stored data in which the combination of coefficients or weighting factors for low and high energy images can be optimized to eliminate motion artifacts and to cancel soft tissue and bone from the resulting image.

In another embodiment of the invention, basically, a low energy image and a high energy pre-contrast image are acquired and their data are stored in separate memories. A low energy post-contrast live image is then made and its data are subtracted in real-time from the stored low energy pre-contrast image data and the difference image is stored as the low energy temporal difference image. Similarly, a high energy post-contrast live image is made, its data are subtracted from the stored high energy pre-contrast image and the difference image is stored as the high energy temporal difference image. Then, to obtain a hybrid subtraction image, the low and high energy temporal difference images are scaled with suitable coefficients and subtracted and stored, displayed or both as the hybrid image.

How the foregoing and other more specific features of the invention are achieved will be evident in the ensuing description of illustrative embodiments of the new apparatus for conducting multiple or hybrid digital subtraction and temporal subtraction in a fluorographic system which will now be set forth in reference to the drawings.

DESCRIPTION OF THE DRAWINGS

FIGS. 5A, 5B and 6A, 6B are timing and sequence diagrams relating to different modes for obtaining temporal and hybrid subtraction images.

DESCRIPTION OF A PREFERRED EMBODIMENT

Figure 1:
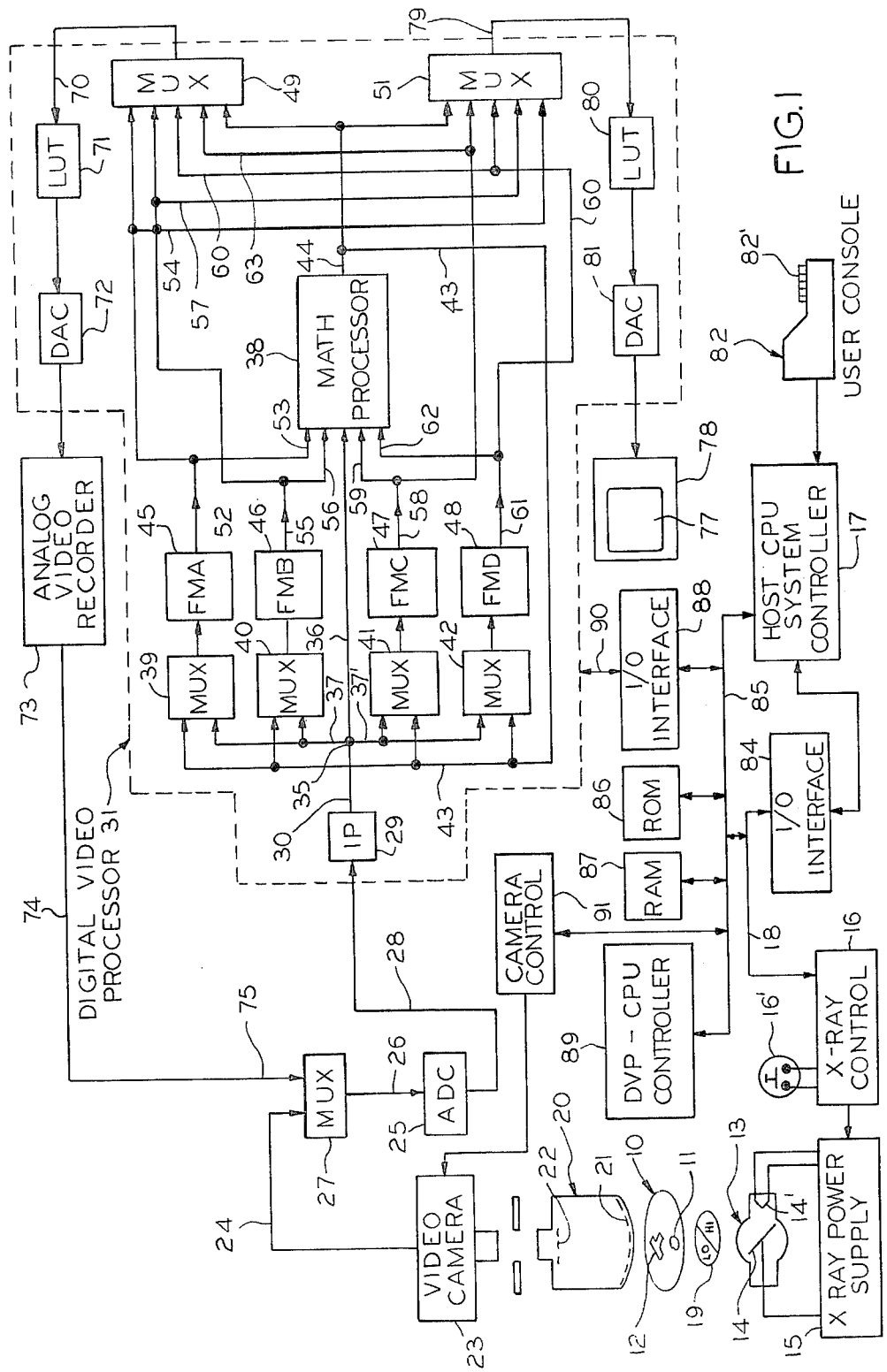
FIG. 1 is a block diagram of apparatus for obtaining temporal and hybrid subtraction images selectively by various operational modes.

The equipment needed to obtain the X-ray images for digital fluorography procedures is shown in the left region of FIG. 1. A patient is represented by an ellipse marked 10. A bony structure in the patient is represented by the configuration marked 11. A blood vessel which might be a renal artery, a carotid artery or the aorta, for example, is marked 12 and is illustrated as being in the same field of view of the bony structure. It is, of course, the ultimate objective of the invention to permit visualization of blood vessels when they are filled with an X-ray contrast medium, such as an iodine compound solution, even though the blood vessel overlays or underlays bone and is surrounded by soft tissue that is subject to movement.

An X-ray tube 13 is used to make the X-ray exposures. The tube has the usual anode or target 14 and an electron beam emitting filament 14'. An X-ray tube power supply 15 contains the components such as a step-up transformer and rectifier for applying a high kilovoltage between the anode 14 and cathode 14' to effectuate emission of a beam of X-ray photons from target 14 through the patient for making an X-ray exposure. The control for the X-ray power supply is symbolized by the block labelled X-ray control and marked 16. A system controller CPU 17, together with some synchronization and timing circuits, not shown, provides timing and synchronization for the system. The system controller CPU 17 has an address/data bus 85 coupling it with an input/output (I/O) interface 84. A read-only memory (ROM) 86 and a random access memory (RAM) 87 are coupled to the bus. The controller will be discussed later as occasion arises. For present purposes it is sufficient to recognize that the system controller CPU 17 supplies signals at appropriate times through I/O interface 84 to the X-ray control 16 by way of a bus 18 which results in the X-ray control causing the X-ray power supply to apply either a low kilovoltage (kV) or a high kilovoltage between the X-ray tube anode 14 and cathode 14'. At each applied kilovoltage, a beam with a spectral distribution of X-ray photon energies is produced. Thus, low kV is used herein to denote low average energy and high kV to denote comparatively high average energy. By way of example, for the purposes of digital fluorography, a typical low average energy X-ray photon spectrum might correspond to an applied X-ray tube peak kilovoltage in the range of 60 to 85 kilovolts and a typical high peak kilovoltage would be in the range of 130 to 145 kilovolts. X-ray tube current levels and X-ray beam intensities are typically those used in radiography. The intervals or durations of X-ray exposures of the high energy or low energy beams are typically in the range of 4 ms to 400 ms by way of example, and not limitation. An illustrative dual kilovoltage and, hence, dual energy X-ray power supply is described in the pending application of Daniels, et al, Ser. No. 208,095, filed Nov. 18, 1980. That application is assigned to the assignee of this application and is incorporated herein by reference.

For digital fluorography, a rotating filter disk 19 is preferably interposed between the X-ray source 13 and patient 10 to filter out the higher spectral band when the low energy X-ray beam is being produced and to filter out the lower spectral portion when the higher energy X-ray beam is being produced. This is done to maximize the difference in spectral distribution between the low and high energy beams. The two halves of the disk 19 are marked lo (low) and hi (high). Examples of the composition of the respective filters were given earlier.

In FIG. 1, the X-ray image entraining beam that emerges from patient 10 during occurrence of either a high energy or a low energy X-ray exposure enters an image receptor such as a conventional electronic X-ray image intensifier which is designated by the numeral 20. X-ray doses are at typical radiographic levels for the subtraction methods described herein as compared to the lower dose levels that are used for fluorography.

Intensifier 20 has a curved photocathode 21 that converts the X-ray image to a fluorescent image and then to an electron image that is focused onto a phosphor screen 22 which converts the electron image into an optical image. A television camera, labelled "video camera" and marked 23 is aimed at screen 22. The analog video signals resulting from conversion by the camera of the optical image are output on a cable 24 to one input of an analog multiplexer (MUX) 27 whose output couples, by way of line 26, to the input of an analog-to-digital converter (ADC) marked 25. For the purposes of the invention, the target, not shown, of the video camera is scanned or read out on a frame-by-frame basis in the progressive scanning mode. Thus, in a television system that is based on 60 Hz power line frequency, an image frame in the video camera is read out or scanned in 1/30 of a second or about 33 ms. The video camera scanning beam is blanked out during an X-ray exposure and there is no readout or scanning until after an exposure is complete. A more comprehensive discussion of the operating mode and characteristics of the video camera may be seen in the pending application of Wesbey, et al, Ser. No. 321,007, filed Nov. 13, 1981. The application referred to is incorporated herein by reference. Said application is assigned to the assignee of this application.

Two video cameras such as the one marked 23 may also be used. A digital fluorographic system in which one camera is used for obtaining the low X-ray energy image and another is used for obtaining the high X-ray energy image is described in a pending application of Georges et al, Ser. No. 229,249, filed Jan. 28, 1981. This pending application is assigned to the same assignee as the present application. Said pending application is incorporated herein by reference.

In the embodiment described herein, wherein one video camera 23 is used, the analog video signals resulting from progressive scanning of the video camera target are converted to digital numbers representative of picture elements (pixels) whose values correspond to the intensity or brightness level of the pixels. The analog video signals are converted or quantitized by analog-to-digital converter (ADC) 25 to a 10-bit digital word per pixel by way of example. The output of ADC 25 is coupled by way of a bus 28 to the input of an input processor (IP) 29 which is an input stage to a digital video processor (DVP) 31 that is contained in the dashed line configuration. IP 29 comprises a look-up table which converts linear digital pixel values coming out of ADC 25 to corresponding logarithmic values that are output from the processor on a bus 30. Bus 30 junctions at a point marked 35 with a bus 36 and two branch buses 37 and 37'. Bus 36 is one input to a math processor that is represented by the block marked 38. The math processor is shown in detail in FIG. 2 and will be discussed later as required. Branch buses 37 and 37' couple to inputs of respective MUXes 39, 40, 41 and 42. Each of these MUXes has another of its inputs coupled to a wraparound bus 43 which connects to the output bus 44 from math processor 38.

Other significant components of the digital video processor (DVP) 31 are four full-frame memories that are labelled FMA, FMB, FMC and FMD and are further identified by the reference numerals 45, 46, 47 and 48, respectively. In what is believed to be a preferred operating mode for the fluorographic system as will be described later, only three full-frame memories are needed but in another useful mode four memories are needed. In this example, full frame memories 45–48 are capable of storing an array of 512×512 digital values corresponding to pixels that compose an image frame.

There are two DVP output MUXes 49 and 51 at the far right in FIG. 1. The output bus 52 from frame memory A (FMA 45) couples to one input 53 of math processor 38 and to the inputs of MUXes 49 and 51 which are coupled to a common bus 54. Similarly, output bus 55 from FMB 46 couples to another input 56 of math processor 38 and to a common bus 57 which also couples to inputs of MUXes 49 and 51. Output bus 58 from FMC 47 couples to math processor input 59 and to a common bus 60 which also couples to inputs of MUXes 49 and 51. Math processor output bus 44 also couples to a corresponding input of MUXes 49 and 51.

Digital data representative of images in any state of processing can be output from any one of the DVP 31 output MUXes 49 and 51. MUX 49, for example, can output image data on its output bus 70 to a look-up table (LUT) 71 and then to a digital-to-analog converter (DAC) 72 wherein the digital pixel data is converted to analog video signals for being recorded in a mass storage device such as on a video magnetic disk recorder symbolized by the block marked 73. As will be evident later, video recorder 73 may be used to store image frame pixel data, in analog signal form, corresponding to low X-ray energy and high X-ray energy images, temporal images and hybrid subtraction images, for example. The video recorder 73 makes it possible to display previously acquired images of any kind and it also permits reprocessing of image data as will be discussed in greater detail later. Thus, the output line 74 from analog video recorder 73 leads to another input 75 of previously mentioned analog signal MUX 27 after which the analog video signals are input to ADC 25 wherein the signals are reconverted to digital pixel values for being fed back into the input processor 29 for reprocessing in DVP 31. Of course, the look-up table, not shown, in the input processor 29 functions in the linear mode at this time since another logarithmic conversion is not required.

Images are displayed on the screen 77 of a television monitor 78. The television monitor is driven by signals derived from output bus 79 of MUX 51. This output bus 79 leads to the input of an LUT 80 which has a transfer function for operating on the digital pixel data to expand it for filling the full dynamic range of the television monitor. After the data are modified in LUT 80 they are directed to a digital-to-analog converter (DAC) 81 wherein the signals are converted to analog video signals for driving television monitor 78.

The user communicates with the system through a user console 82 that has a keyboard 82' for input of user requests. Timing, control, and transfer and manipulation of data in the system is described in more detail in a pending application of Andrews, et al, Ser. No. 321,307, filed Nov. 13, 1981. The application is assigned to the assignee of this application and is incorporated herein by reference.

A description of the controls in sufficient detail for understanding the present invention is as follows. Programs for executing various X-ray techniques including basic image data acquisition, temporal subtraction, hybrid subtraction and data reprocessing and so forth are stored in the memory, not shown, of host CPU system controller 17. System controller 17 responds to user requests from console 82 by sending an instruction set, called a recipe, to a random-access memory (RAM) 87 by way of an input-output (I/O) interface module 84 and a bidirectional address/data bus 85. A read-only memory (ROM) 86, an I/O interface 88 and a digital video processor-CPU, (DVP-CPU) controller 89 are also coupled by way of buses to bus 85. DVP-CPU controller 89 interprets the recipe, using an interpreter program stored in ROM 86, and sets up various components of the system to perform the functions required for executing the recipe. For example, the input processor 29 of the digital video processor 31 may be set to operate in a linear mode or a logarithmic translation mode. Various multiplexers such as MUXes 27, 39–42, 49 and 50 may be selectively enabled or disabled. The frame memories 45–48 may be set to be read out or written into. The math processor 38 may be set to operate in selected modes. These components, and others in the system which were not recently mentioned, have registers, not shown, that receive code words from DVP-CPU controller 89 in which bits are set or not set to control the component or alter data paths as required. The buses for transmitting operational code words to the registers of the components are not shown individually but are symbolized collectively by the bus segment 90 which couples to I/O interface 88. As explained in the above-cited application of Andrews, et al, no change is made in the data paths within DVP 31 while image data are being acquired. Data paths are only altered during vertical blanking intervals of the video camera 23. The hardware in the presently disclosed system is arranged differently than in the cited application so that the temporal and hybrid image subtraction processes mentioned earlier can be accomplished.

Generally, after the system is initialized for executing a recipe in response to a user requested X-ray technique, X-ray image data acquisition does not begin until a manually operated switch 16', coupled to X-ray control 16, is closed momentarily. X-ray will only go on if the DVP-CPU controller 89 has provided an enabling or ready signal code to X-ray control 16 by way of bidirectional bus 18 so that all functions of the system stay in proper time relationship. A camera control interface or module 91 is coupled to the DVP-CPU controller bus 85 and the video camera for controlling the video camera 23. For instance, the target of the camera is blanked during an X-ray exposure and is read out in the progressive mode during a frame time following an exposure as will be discussed later.

Figure 2:
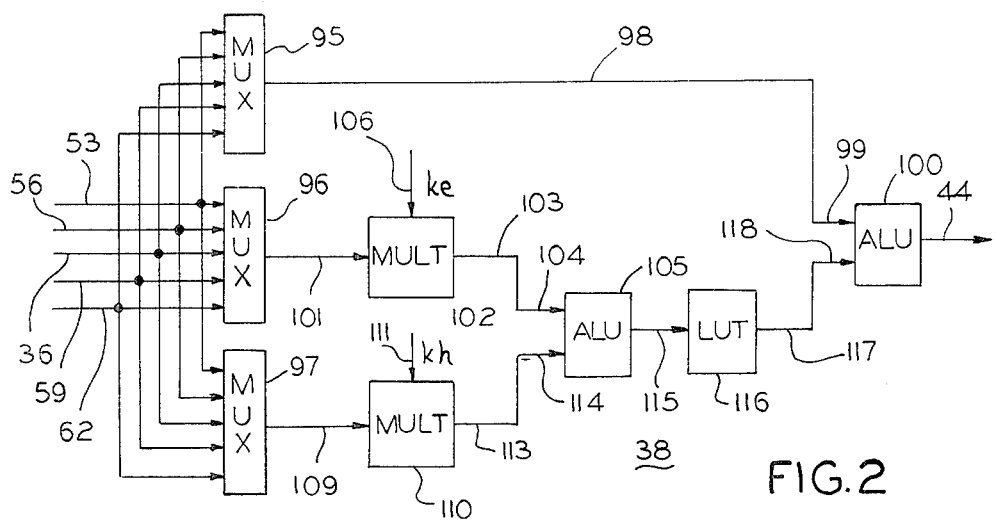
FIG. 2 is a more detailed block diagram of a math processor that is represented by a single block in FIG. 1.

The principal components of math processor 38 of FIG. 1 are shown in FIG. 2. The math processor comprises MUXes 95, 96 and 97. These MUXes are shown to have five inputs for any of them or all of them to receive data by way of buses 53, 56, 36, 59 and 62 which were identified earlier in connection with FIG. 1. A 12-bit bus 98 couples the output of MUX 95 to one input 99 of an arithmetic logic unit (ALU) 100. A bus 101 couples the output of MUX 96 to the input of a multiplier (MULT) 102. A bus 103 couples the output of MULT 102 to one input 104 of an ALU 105. MULT 102 has another input bus 106. A digitally expressed weighting or scaling factor $k_l$ can be input to MULT 102 through bus 106 from DVP-CPU 89 for the purpose of permitting the image data supplied through input bus 101 of MULT 102 to be multiplied by $k_l$ (k sub ell) when required. $K_l$ is a weighting or scaling factor for low X-ray energy image data.

A bus 109 couples the output of MUX 97 to an input of another MULT 110. A bus 111 facilitates providing to MULT 110 a weighting factor $k_h$ from DVP-CPU 89 for image data that is obtained at high X-ray energy. A bus 113 couples the output of MULT 110 to the other input 114 of ALU 105. The output of ALU 105 is coupled, by way of a bus 115 to the input of a look-up table (LUT) 116 which has a transfer function for producing a gain as required. The output of LUT 116 is coupled, by way of a bus 117, to the other input 118 of ALU 100. Output bus 44 from ALU 100 corresponds to the similarly marked bus at the output of math processor 38 in FIG. 1.

It should be noted that the low and high energy coefficients or weighting factors $k_l$ and $k_h$ can be input to multipliers 102 and 110, respectively, as required. In an actual embodiment, it is contemplated to allow the user to apply different weighting factor values to the image data by way of MULTS 102 and 110 of the math processor 38 while watching the images being presented on the screen of television monitor 78. A choice of weighting factors allows the user to select the one that results in the preferred cancellation of bone or soft tissue in the displayed image. Different weighting factors can be stored in host CPU 17 memory and selected with the user console keyboard 82'. In the embodiment of the invention that uses the three memories FMA, FMB and FMC, a key switch is provided that allows the user to vary the values of $k_l$ and $k_h$ to any value that produces optimal cancellation during image reprocessing. In the embodiment that uses four memories FMA, FMB, FMC and FMD, $k_l$ and $k_h$ values are selected before the procedure is started but may also be varied during reprocessing.

Figure 3:
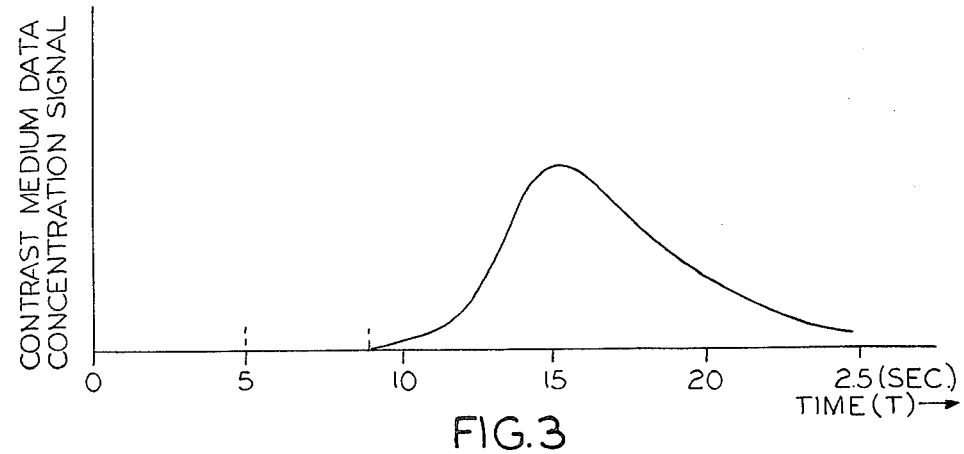
FIG. 3 is a typical or illustrative graph of contrast medium concentration or density versus time after the medium is injected intravenously.

Refer now to FIG. 3 which is an illustrative plot of how concentration of an X-ray contrast medium in a blood vessel might vary with time. In this example, it is assumed that the contrast medium was injected intravenously at time zero. In a little less than 10 seconds blood with contrast medium mixed in it is beginning to enter the blood vessels in the region of interest. At about 15 seconds the contrast medium density is maximum and it becomes more dilute as time progresses toward 25 seconds. In other cases more or less time may elapse between injection, arrival and departure of contrast medium.

Figure 4:
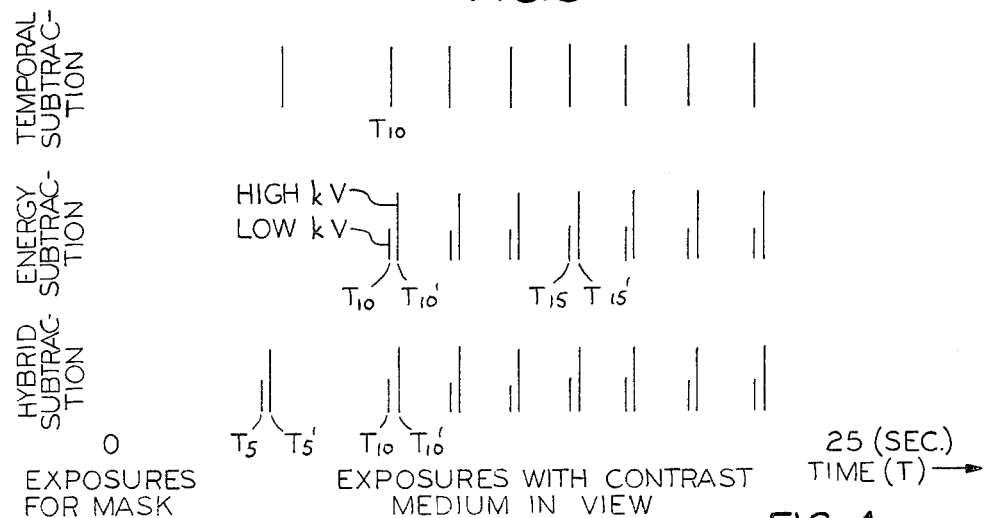
FIG. 4 is a diagram used for discussing the characteristics of and differences between temporal, energy and hybrid subtraction on a time scale.

FIG. 4 is for demonstrating the basic difference between temporal, energy and hybrid subtractions.

In temporal subtraction in FIG. 4, an X-ray exposure is made before the contrast medium arrives such as at about 5 seconds (per FIG. 3) with a radiographic level kilovoltage applied to the X-ray tube target to obtain the pixel data for a mask image which is stored. Then at $T_{10}$ a sequence of exposures, typically at about one second intervals are begun at a post-injection time when the contrast medium is expected to have reached the vessels of interest. The image data for the post-injection sequence are assumed to be stored as they are acquired. One post-injection image after another is then typically subtracted from the mask image to cancel anything that is common to the pre-injection mask and post-injection images and let the contrast medium filled vessels remain. The difference images are displayed consecutively in an effort to find the one that shows the blood vessels with the highest contrast and resolution or sharpness. This is not necessarily the image that was obtained at maximum contrast medium concentration.

Still referring to FIG. 4, in energy subtraction one or more pairs of low and high kV X-ray exposures, that is, low and high average energy exposures are made beginning slightly before or after the contrast medium reaches the blood vessels being studied. For example, a sequence of low and high energy exposure pairs may be initiated with a low energy exposure at $T_{10}$ and a high energy exposure at $T'_{10}$ and may continue past the peak contrast medium concentration at $T_{15}$. Typically, a low energy exposure is made within a televison frame time of 33 ms while readout of the video camera target is blanked. The target may be read out during the next frame while the image frame is concurrently being digitized as pixel data and stored. The high energy exposure for the pair is made during the next frame and read out during the following frame and the resulting live high energy digitized pixel data may be subtracted from corresponding low energy stored data to produce a difference image frame that can be stored on disk with others in the sequence for subsequent display. In energy subtraction, the data for one or the other or both of the low and high energy are scaled to bring about cancellation or subtraction out of soft tissue which is common to both images. However, scaling to cancel bone results in some undesirable cancellation of the contrast medium in the vessels, too. Signal-to-noise ratio is also reduced. An advantageous feature of energy subtraction is that the low and high energy images in a pair are obtained so close to each other in time that involuntary tissue movement will not cause significant loss of registration between images. In energy subtraction, there can be substantial body motion between high and low energy exposure pairs without harmful effects.

Two new methods of performing hybrid subtraction will be described in connection with FIG. 4. One method involves making a low energy and a high energy exposure pair in quick succession prior to arrival of the contrast medium such as at time $T_5$. These exposures are usually made within a few television frame times so there can be little body movement. A series of such pairs may be made at one second intervals. The two images in a closely successive pair are combined or subtracted and the resulting pre-contrast difference images are stored. The pixel data for these images is scaled or operated on by coefficients before subtraction to effect cancellation of soft tissue and let bony structures remain. When contrast medium arrives, such as at $T_{10}$ seconds, a series of closely successive low and high energy exposure pairs are made. The data for these images are scaled, using the same scaling factors as before, and then subtracted to produce a post-contrast difference image or images wherein soft tissue is cancelled again and bony structures and contrast medium containing vessels remain. Then any of the post-contrast difference images is subtracted from any of the pre-contrast difference images to cancel anything that is common to both of them such that the respective images of the contrast medium-filled vessels remains.

Another hybrid subtraction method which is preferred in accordance with the invention involves making low and high energy exposures in quick succession prior to arrival of the contrast medium such as starting at $T_5$ in FIG. 4 and using the low energy exposure image subsequently as a mask for a temporal subtraction image. Similar low and high energy exposure pairs are made when contrast medium arrives. Then, any post contrast low energy image can be subtracted from any of the pre-contrast low energy images to produce a temporal difference image for display without using scaling factors. However, the image data are handled and made available for processing or reprocessing in such manner that hybrid subtraction images can be produced. If the temporal image or images exhibit low noise, good registration and contrast resolution, the hybrid images need not be produced. If hybrid subtraction images seem to be desirable there is a high probability, that with the image data in storage, some combination of pre-contrast and post-contrast images will yield a hybrid subtraction image that is satisfactory enough for diagnostic purposes to obviate the need for retaining the patient to repeat the procedure.

Typically, for digital subtraction methods, the low and high energy X-ray exposures will be made at radiation intensities or X-ray tube currents corresponding to those used in ordinary radiography. By way of example and not limitation, each high and low energy exposure will typically have a duration in a range of 4 to 400 ms. Short exposures, less than a television frame time of 33 ms are most effective to stop motion. Generally, contrast medium will arrive in the vessels of interest about 3 to 20 seconds after injection. In most procedures that are performed with the disclosed apparatus, the pixel data for previously obtained low or high energy images may be stored temporarily in memory devices. Images obtained subsequently are, during their acquisition time, called live images for convenience. It should be evident that, where energy subtraction is involved, the low energy exposure in a pair does not necessarily have to precede the high energy exposure. The order can be reversed as long as the data are properly handled. One or the other can be made first in any pair.

The mathematical background for hybrid and temporal subtraction methods will now be examined. For hybrid subtraction where the pixel data are converted to logarithmic values the pre-contrast or mask images are expressed as follows:

$$M_l = \mu_{l,t} x_t + \mu_{l,b} x_b \qquad \text{(Eq. 1)}$$

$$M_h = \mu_{h,t} x_t + \mu_{h,b} x_b \qquad \text{(Eq. 2)}$$

and the post-contrast or live images are expressed as follows:

$$L_l = \mu_{l,t} x_t + \mu_{l,b} x_b + \mu_{l,i} x_i \qquad \text{(eq. 3)}$$

$$L_h = \mu_{h,t} x_t + \mu_{h,b} x_b + \mu_{h,i} x_i \qquad \text{(Eq. 4)}$$

where M and L mean mask and live, respectively, the lower case subscripts "l" and "h" imply the low energy and high energy beams, respectively; and the subscripts "t", "b" and "i" identify the materials tissue, bone and iodine contrast medium, respectively. X-ray linear attenuation coefficients are denoted by "$\mu$" (mu) and the thickness of the material in the beam by "x".

Weighted or scaled combinations of images at low and high X-ray energy are expressed as follows:

$$M = k_l M_l + k_h M_h \qquad \text{(Eq. 5)}$$

$$L = k_l L_l + k_h L_h \qquad \text{(Eq. 6)}$$

where M is the result of combining or subtracting the low energy and high energy pre-contrast or mask image pairs and L is the result of combining or subtracting the live post-contrast low energy and high energy image pairs. The "k's" are coefficients or multiplication factors that can be adjusted to bring about cancellation of material of any density when the algebraic subtractions in equations (5) and (6) are performed. These factors can be optimized by determining their values by experimental measurements or, as previously indicated, means can be provided for allowing the user to try various values of "k", so that when the subtraction images are being displayed the user can try one after another to see which one results in an image of the blood vessels in which artifacts are cancelled out best and which has the best contrast of the vessels containing contrast medium. The k factors in equations (5) and (6) are chosen to bring about subtraction or cancellation of soft tissue.

The combination factors can be chosen to cancel pixel values due to soft tissue. When equations (1) and (2) are inserted into equation (5), the result is:

$$M = (k_l \mu_{l,t} + k_h \mu_{h,t}) x_t + (k_l \mu_{l,b} + k_h \mu_{h,b}) x_b \qquad \text{(Eq. 7)}$$

indicating that tissue cancellation can be achieved by equating the coefficient of $x_t$ (thickness of tissue) to zero. The ratio of combination coefficients for tissue's cancellation is thus:

$$\frac{k_h}{k_l} = \frac{-\mu_{l,t}}{\mu_{h,t}} \qquad \text{(Eq. 8)}$$

The same ratio is used for both mask and live images. Substituting equations (1), (2), (3) and (4) into equations (5) and (6) and using equation (8) yields $$M = k_l \left[ \mu_{l,b} \frac{-\mu_{l,t}}{\mu_{h,t}} \mu_{h,b} \right] x_b \qquad \text{(Eq. 9)}$$

$$L = k_l \left[ \mu_{l,b} \frac{-\mu_{l,t}}{\mu_{h,t}} \mu_{h,b} \right] x_b + k_l \left[ \mu_{l,i} \frac{-\mu_{l,t}}{\mu_{h,t}} \mu_{h,i} \right] x_i \qquad \text{(Eq. 10)}$$

The final step in the hybrid method is a "temporal" subtraction of the energy subtracted mask and live images to remove bone shadows.

$$\text{Thus: } D = M - L \qquad \text{(Eq. 11)}$$

$$= k_l \left[ \mu_{l,i} \frac{-\mu_{l,t}}{\mu_{h,t}} \mu_{h,i} \right] x_i$$

where D is the hybrid difference image data in which pixel values representative of both bone and tissue have been cancelled or subtracted out.

When equation (11) is directly expressed in terms of equation (5) and equation (6), the result is:

$$D = k_l M_l + k_h M_h - k_l L_l - k_h M_h \qquad \text{(Eq. 12)}$$

$$= k_l (M_l - L_l) + k_h (M_h - L_h)$$

$$= k_l T_l + k_h T_h$$

where $T_l$ and $T_h$ represent the low and high energy temporal difference or subtraction images, respectively. Thus, for linear hybrid subtraction the order in which the energy and temporal subtractions is performed is immaterial.

In accordance with one feature of the invention, by operating the apparatus shown in FIG. 1 in a particular mode, the coefficients ($k_l$ and $k_h$ or $k_h/k_l$) need not be determined nor used during acquisition of the low and high energy mask and the low and high energy live image data. An adjunct of this is that a temporal subtraction image is displayed on television screen 77. If in the temporal subtraction image there are not significant soft tissue motion artifacts, and the contrast medium filled vessels are clearly delineated, proceeding with hybrid subtractions may be unnecessary. The temporal subtraction image data in this case, in accordance with the invention, is simply the result of subtracting the post-contrast low X-ray energy image data ($L_l$) from the pre-contrast or mask low X-ray image data ($M_l$). The resulting low energy difference image has the merit of having higher SNR compared to any of the hybrid image combinations. If the need for the hybrid subtraction method is indicated, this method is carried out in a reprocessing mode wherein the coefficients (k) are used, in accordance with the invention.

An illustration of the modes of operation discussed in the preceding paragraph will now be given in reference to FIGS. 1 and 3 and the FIG. 5 timing diagram which is comprised of parts 5A and 5B. Part A of FIG. 5 is the timing sequence of the X-ray exposures and TV camera readout and part B is the timing sequence of the video processor. First, the digital pixel data for a mask image must be obtained in two steps.

(1) Make a low X-ray energy (low kV) pre-contrast exposure during TV frame 1 in FIG. 5A while the camera readout is blanked, read out or scan the video or TV camera 23 target in the progressive scan mode during the next frame 2, store the resulting digital pixel data in full frame memory FMA of FIG. 1.

(2) Make a high energy (high kV) pre-contrast exposure during frame 3 in 5A immediately after the camera readout of the low kV exposure. Then scan the camera target in the progressive mode and store the resulting digital data in FMB. Scrub the TV camera tube target during ensuing frame 5 of 5A.

Then acquire the post-contrast images, beginning at the time the contrast medium is expected to reach the blood vessels of interest as follows:

(3) Make a low energy post-contrast exposure during a first TV frame 1 in FIG. 5A while the TV target is blanked and scan the camera target in the progressive mode during the next frame 2 in FIG. 5A. Feed the live digital pixel data for this image into the math processor 38 by way of bus 36 while simultaneously feeding the stored low kV pre-contrast pixel data from FMA to the math processor by way of its input 53. Have the math processor make subtractions of corresponding pixels in ALU 105 of live low energy post-contrast pixel data from the stored low energy pre-contrast data and output the resulting low energy temporal difference image data on bus 44.

(4) Read back the temporal subtracted difference image data by way of bus 43 and MUX 41 for storage in a progressive scan format in FMC as the low energy temporal difference image as indicated by the interval marked 6 in part B of FIG. 5. When FMC is loaded, read out the odd numbered horizontal lines of pixel data and then the even number lines of pixel data from FMC at video rates. In other words, effect a scan conversion by reading out FMC in the interlaced mode and feeding via buses 58 and 63 to MUX 49 and to LUT 71 via bus 70 and DAC 72 for storage of the low kV temporal image in disk recorder 73 in analog interlaced image format as indicated at interval 7 in part 5A of FIG. 5. Also feed the low energy temporal image contents from FMC in the interlaced mode to output MUX 51 and then LUT 80 and DAC 81 to be displayed on TV screen 77 in analog interlaced image format.

(5) Make a high energy post-contrast live exposure immediately after the camera readout of the last low energy live post-contrast exposure as in frame 3 in FIG. 5A, and scan the camera target in the progressive mode as in frame 4 and scrub the TV camera as in frame 5. Use ALU 105 in the math processor to subtract this high energy post-contrast live image pixel data from the pre-contrast mask image pixel data that was stored in FMB in step 2 above. Store the resulting high energy temporal difference image data in FMC in progressive scan format as in interval 8 in FIG. 5B. As in preceding step 4, read out FMC in the interlaced mode and output through MUX 49, LUT 71 and DAC 72 for storage in disk recorder 73 as the high energy temporal difference image in interlaced format as in interval 9 of 5B.

Steps 3 to 5 may be repeated several times to acquire additional low energy and high energy temporal difference images and to store them in interlaced format in analog video recorder 73. Refer to FIG. 3 which is a typical plot of the concentration of the contrast medium in the blood vessels of interest versus time. As an example, the precontrast high and low energy mask image data could be obtained at time zero or at any time up to about 9 seconds after contrast medium injection. The post-contrast exposures could have been initiated just prior to 9 seconds when the contrast medium was not yet in the X-ray field of view. Hence, a sequence of high and low energy post-contrast image pairs are made at one second intervals, for example. At the 9th second, a small amount of contrast medium appeared. Images obtained around the 15th second would exhibit peak contrast. The peak contrast low and high energy image data may or may not be the best to subtract from the stored low and high energy pre-contrast mask, respectively. For instance, the peak contrast post-contrast images might have artifacts due to soft tissue motion. Post-contrast data obtained before or after peak contrast might have fewer artifacts and have better registry with the pre-contrast low and high energy image data so it would be more desirable to use the less than peak contrast data for producing the temporal difference images. An alternate pre-contrast mask image or one below peak contrast in the post-contrast range may also be selected and any one of the post-contrast high energy combined with it in an effort to find a temporally subtracted image with optimum contrast. Selection of an alternate mask can, however, only remove motion artifacts if the motion in it happens to match the motion in the selected post-contrast image. One reason for trying to settle for the best obtainable temporally subtracted image is that such image will ordinarily have optimum signal-to-noise ratio (SNR).

It has been discovered that the signal-to-noise ratio of the final low energy temporal difference image or images can be further improved, provided soft tissue motion does not cause significant artifacts or if no soft tissue motion was present in the low energy temporal difference image. The improvement is achieved, in what becomes a final image, relative to the low energy temporal difference image alone by adding, not subtracting, some weighted or scaled version of the low energy temporal difference image to a high energy temporal difference image. The low energy temporal image is given the weight relative to the high energy image because most of the information one would desire to get out is in the low energy temporal difference image. The latter has the better contrast. Of course, because of the image acquisition and disk storage sequence used in the steps set forth above, several low and high energy temporal difference images will be on disk, so any low energy temporal difference images can be weighted and added to any high energy temporal difference image as in the preceding paragraph to get the final image with the best contrast medium contrast.

If a temporally subtracted image free of motion artifacts is not found, carrying out the hybrid subtraction method is indicated. Hybrid subtraction is totally immune to soft tissue motion because soft tissue is completely subtracted out when the low and high images are subtracted. Moreover, bone has been cancelled already as a result of the previous temporal subtracted exposures that resulted in the difference images. The SNR for hybrid subtraction is typically about one-half of the SNR for temporal subtraction. Hence, it is equivalent to choosing an alternate mask, as in the preceding paragraph, that is no closer than about 3 seconds to the peak contrast image. It turns out, that insofar as motion stoppage is concerned, hybrid subtraction is 50 to 100 times better for the same SNR that would be obtained with temporal subtraction.

In accordance with the invention, after the imaging sequence discussed above is completed, data for several low energy and several high energy temporal difference image frames will be stored as analog video signals on disk recorder 73 in interlaced format. Any of these temporal subtraction images can be displayed on television monitor 78. The low kV temporal subtraction images, since they have the highest SNR, are preferably displayed in sequence to determine which one has resulted in the most complete cancellation of bone such as to show the blood vessels with greatest contrast. If the presence of soft tissue motion artifacts indicates that the hybrid subtraction method should be undertaken, no additional exposures are necessary since, in accordance with the invention, all of the data for hybrid subtraction is stored on analog video disk already. Hybrid subtraction simply requires reprocessing of the infoready stored on magnetic disk in analog recorder 73 as will be discussed in greater detail later.

For display of the low energy temporal subtraction images to inspect them as just discussed, the interlaced analog signals representing each of them are output on bus 79 to ADC 25 where they are reconverted to digital signals again. The digital pixel signals are then fed through digital video processor 31 without modification and are output from MUX 51 by way of bus 79 to LUT 80 and DAC 81 for conversion to analog video signals that drive television monitor 78. Display of the stored temporal images in sequence can be called for by using keyboard 82' of console 82. Now for hybrid subtraction, the image pixel data resulting from subtracting any low energy post-contrast image from the low energy pre-contrast image, that is, the low energy temporal subtracted image data, is retrieved from analog disk recorder 73, and after being digitized again, is stored in FMA. The low energy temporal subtraction image obtained with maximum contrast medium in view is the preferred one to use usually. This low energy temporally subtracted image data will be stored in FMA for being read out in the interlaced mode since it was previously stored on disk in recorder 73 in this mode.

With FMA filled, the data for the corresponding high energy temporal image may be recalled from disk and held in FMB for being combined in pixel correspondence with the low energy temporal difference image, using the math procesor 38. What must be done in procesor 38 is to combine the low energy and high energy temporal images according to Equation 12. In these images stationary soft tissue and bone have already been cancelled, leaving only images of contrast medium filled vessels and artifacts due to soft tissue motion. To eliminate these artifacts, the pixel data representative of the low energy combination must be multiplied by a suitable coefficient, $k_l$, and the high energy combination must be multiplied by a suitable coefficient, $k_h$, to bring about soft tissue cancellation. Thus, the image data from FMA is fed to MULT 102 in the math processor 38 where each pixel value is multiplied by $k_l$ and the data from FMB are fed in correspondence to MULT 110 where the data are multiplied by $k_h$. The corresponding pixel data from MULTs 102 and 110 are then subtracted in ALU 105. Then gain and offset are introduced in LUT 116 and ALU 100 and the data are output on bus 44 of the math processor as the hybrid subtraction digital pixel data. The pixel data may be fed through video processor output MUX 51 and converted to analog video signals for permitting display of the hybrid subtraction image on televison screen 77. The hybrid subtraction pixel data can also be fed out of MUX 49 of the video processor 31 for being converted to analog video signals and stored in disk recorder 73 for future display if desired.

As shown by equation 8, soft tissue cancellation, which is most important because tissue movement is a significant cause of misregistration artifacts, can be obtained by choosing a ratio of k's equivalent to the right side of equation 8. This ratio can be used as a first approximation. As previously explained, different coefficient values can be made available to the user. Thus, the raw data from FMA and FMB can be acted upon by a variety of coefficients repeatedly to allow the user to determine, by observing the television screen 77, which hybrid image shows the contrast medium filled vessels with the best contrast and resolution. Moreover, since it is assumed that a sequence of low energy and high energy temporal images have been made, any of them can be retrieved from the analog video recorder for processing as described earlier in this paragraph, so that the best hybrid subtraction image can be selected. The image data reprocessing procedures are, of course, carried out without the need for making any additional X-ray exposures.

The method described above was performed with apparatus comprised of three full frame memories, FMA, FMB and FMC. Another method that allows display of either the low kV temporal difference image or the hybrid difference image during acquisition, and storage of these images during acquisition uses an alternative embodiment of the apparatus wherein four full frame memories, FMA, FMB, FMC and FMD, the latter being numbered 48, are required as shown in FIG. 1. With this method, hybrid subtraction images become available without having to reprocess previously acquired temporal difference images. The hybrid images are developed during the acquisition process. The alternative apparatus arrangement and method will be described primarily in reference to FIGS. 1 and 3 and the FIG. 6 timing diagrams in parts 6A and 6B of the latter figure.

As in the previously discussed embodiment, the first operation is to acquire a mask image in two steps:

(1) Make a low energy pre-contrast X-ray exposure as in frame 1 in part 6A of FIG. 6 with the TV camera target blanked, read out the target of video camera 23 in the progressive scan mode after the exposure is terminated as in frame 2 of 6A and store the resulting digital pixel data in full frame memory FMA.

(2) At the beginning of the first frame interval following readout of the low energy image, make a high energy pre-contrast X-ray exposure, read out the target of video camera 23 in the progressive scan mode during the frame after the exposure is terminated as in frame 4 of 6A and store the resulting digital data in memory FMB. During the next frame 5, scrub the TV camera target.

After the previous two steps are completed and usually after several seconds have elapsed, a sequence of post-contrast image frames are made beginning slightly before the contrast medium is expected to reach the blood vessels, such as just prior to 5 seconds in FIG. 3, as follows:

(3) Make a low energy X-ray exposure during frame 1 in 6A and read out the target of video camera 23 in the progressive scan mode after the exposure is terminated as in frame 2. As the resulting realtime or live low energy post-contrast digital pixel are being produced, and as indicated by coincident frame 2 in 6A and interval 6 in 6B, subtract the same in the progressive mode from the low energy pre-contrast data stored in FMA, using ALU 105 in the math processor. Store the results of each corresponding pixel subtraction successively in FMC in the progressive format as indicated in interval 6 of 6A as a low energy temporal difference image.

(4) Immediately after camera readout of the preceding low energy post-contrast exposure, make a high energy post-contrast X-ray exposure as in frame 3 of 6A. During the high energy exposure read the low energy post-contrast temporal subtracted image from FMC in the interlaced format and store the result on video disk 73, as per frame 3 of 6A and interval 7 of 6B.

(5) Read out the target of video camera 23, during the frame after the high energy post-contrast exposure is terminated as in frame 4 of 6A, in the progressive scan mode. As the resulting realtime or live post-contrast digital pixel data are being produced or read out from the target in the progressive mode as in frame 4 of 6A, subtract the same in the progressive mode from the corresponding high energy pre-contrast pixel data previously stored in FMB using ALU 105 in the math processor. Store the results of each corresponding pixel subtraction in memory FMD in progressive format as the high energy temporal difference image. Scrub the target.

(6) Read the low energy temporal difference image data out of memory FMC in the interlaced mode while simultaneously reading the high energy temporal difference image data out of the fourth memory FMD in the interlaced mode and input the low energy temporal difference image data read from FMC to MULT 102 of the math processor and the high energy temporal difference data from FMD to MULT 110 simultaneously. In MULT 102 multiply the data by the scaling coefficient $k_l$ and in MULT 110 multiply by the coefficient $k_h$ to bring about soft tissue cancellation. Input the data that has been operated on by the coefficient in MULTs 102 and 110 simultaneously to ALU 105 for subtraction of one set of data from the other and store the results on analog video disk as the hybrid subtraction image which is in interlaced format already.

All of the procedures in steps 3 through 6 should be repeated to obtain additional post-contrast images for assuring that one or more is obtained when contrast medium density is maximum or near maximum. The low and high energy pre-contrast image data are retained in FMA and FMB, respectively, so the hybrid subtraction process can be carried out repeatedly even though this results in writing over the data in FMC and FMD. However, there is no loss since all of the previous hybrid subtraction images have been stored on disk and so have all of the low energy temporal subtraction images.

Although it was not stated in the sequence of operations just outlined, the low energy temporal difference images are displayed on the television screen as they are being produced. Moreover, after a procedure is completed, the low energy temporal difference images can be recalled from disk and viewed in sequence to find the image that is optimized for contrast in the blood vessels. If the contrast-filled blood vessels are obscured by soft tissue motion artifacts, the corresponding hybrid subtraction image can be selected from the disk recorder as the best image from the study.

Although illustrative embodiments of the invention have been described in detail, its true scope should be determined by interpreting the claims which follow.

We claim:

1. A method of producing a visible image of a body region defined by the X-ray contrast medium it contains wherein:

pre-contrast X-ray exposures are made before the medium enters the region and post-contrast exposures are made after it enters; pairs of exposures are made in succession with low and high average energy X-ray beams in either order; an image resulting from an exposure is formed on the target of a television camera; and, analog video signals resulting from scan readout of said target are converted to digital logarithmic data representative of picture elements composing a frame; said method including the following steps:

make a selected one of a low energy or a high energy pre-contrast X-ray exposures in a pair and after the exposure ends read out said target in the progressive scan mode and store the digital pixel data for the resulting image frame in one memory and after readout is complete make the other of said exposures in the pair and after the exposure ends read out said target in the progressive scan mode and store the digital pixel data for the resulting image frame in another memory, make a selected one of a low energy or a high energy post-contrast exposures in a pair and read out said target in the progressive scan mode while concurrently combining by subtraction the digital pixel data for this image frame with the corresponding stored digital pixel data for said pre-contrast image made at the same energy and store the resulting difference image data in a third memory, read out the third memory and store the difference image data in a mass storage device as one of the temporal difference images obtained with the same high or low X-ray energy, make the other of the low energy or high energy post-contrast exposures in the pair and read out said target in the progressive scan mode while concurrently combining by subtraction the digital data for this image frame with the corresponding stored digital data for said pre-contrast image made at the same energy and store the resulting difference image data in said third memory as the other of the temporal difference images obtained with the same but other of the high or low X-ray energies, and read out said third memory again and store the data in said mass storage device as the other of the temporal difference images obtained with the same low or high X-ray energy, such that there is data representative of at least one low energy temporal difference image and data representative of at least one high energy temporal difference image in storage, retrieve from said mass storage the data for one or more of the temporal difference images corresponding to the low X-ray energy and convert said data to signals suitable for driving a television monitor, display thelow energy temporal difference images one at a time for enabling the images to be examined for artifacts, based on the examination elect to either not produce or to produce hybrid subtraction images, if production of hybrid subtraction images is elected, retrieve from said mass storage the data for a stored temporal difference image corresponding to one X-ray energy and also retrieve the data for a stored temporal difference image corresponding to the other X-ray energy, multiply said temporal difference images data by predetermined weighting coefficients, respectively, and combine the data resulting from the multiplications to thereby produce a data set representative of a hybrid subtraction image, convert the data set to signals suitable for driving a television monitor, to display the hybrid subtraction image.

2. The method as in claim 1 wherein the digital temporal difference image data in said third memory are read out each time in the interlaced mode and said digital temporal difference image data are converted to corresponding analog video signals and then stored in said mass storage device.

3. The method according to any of claims 1 or 2 including making additional pairs of closely successive low energy and high energy post-contrast exposures to produce for storage in said mass storage a series of low energy temporal difference image data sets and high energy temporal difference image data sets.

4. The method according to any of claims 1 or 2 including the step of using the low energy temporal difference image data as it is being read out of said third memory to drive television means for displaying said low energy temporal difference image.

5. The method according to claim 1 wherein after the image on said target resulting from an exposure at one X-ray energy is read out, said target is scrubbed for at least one television frame before an exposure at the other X-ray energy is made.

6. A method of producing a visible image of a body region defined by the X-ray contrast medium it contains wherein:

pre-contrast X-ray exposures are made before the medium enters the region and post-contrast exposures are made after it enters; pairs of exposures are made in succession with low and high average energy X-ray beams in either order; an image resulting from an exposure is formed on the target of a television camera; and, analog video signals resulting from scan readout of said target are converted to digital logarithmic data representative of picture elements (pixels) composing a frame; said method including the following steps:

make a selected one of a low energy or a high energy pre-contrast X-ray exposures in a pair and after the exposure ends read out said target in the progressive scan mode and store the digital pixel data for the resulting image frame in one memory and after readout is complete make the other of said exposures in the pair and after the exposure ends read out said target in the progressive scan mode and store the digital pixel data for the resulting image frame in another memory, make a selected one of a low energy or a high energy post-contrast exposures in a pair and read out said target in the progressive scan mode while concurrently combining by subtraction the digital pixel data for this image frame with the corresponding stored digital pixel data for said pre-contrast image made at the same energy and store the resulting difference image data in a third memory, read out the third memory and store the difference image data in a mass storage device as one of the temporal difference images obtained with the same high or low X-ray energy, make the other of the low energy or high energy post-contrast exposures in the pair and read out said target in the progressive scan mode while concurrently combining by subtraction the digital data for this image frame with the corresponding stored digital data for said pre-contrast image made at the same energy and store the resulting difference image data in said third memory as the other of the temporal difference images obtained with the same but other of the high or low X-ray energies, and read out said third memory again and store the data in said mass storage device as the other of the temporal difference images obtained with the same low or high X-ray energy, such that there is data representative of at least one low energy temporal difference image and data representative of at least one high energy temporal difference image in storage, and using the data signals representative of a low energy temporal difference image to drive television means for displaying said said low energy temporal difference image and permitting a visual determination of whether significant artifacts are present in the displayed image due to soft body tissue motion, and if such artifacts are absent, weighting said low energy temporal difference image data and adding it to the corresponding data for a high energy temporal difference image to produce a final image data set in which signal-to-noise ratio is improved over the low energy temporal image alone.

7. A method of producing a visible image of a body region defined by X-ray contrast medium it contains wherein:

pre-contrast X-ray exposures are made before the medium enters the region and post-contrast exposures are made after it enters; pairs of exposures are made in succession with low and high average energy X-ray beams in either order; an image resulting from an exposure is formed on the target of a television camera; and, analog video signals resulting from scan readout of said target are converted to digital logarithmic data representative of picture elements (pixels) composing a frame; said method including the following steps:

make a selected one of a low energy or a high energy pre-contrast X-ray exposures in a pair and after the exposure ends read out said target in the progressive scan mode and store the digital pixel data for the resulting image frame in one memory and after readout is complete make the other of said exposures in the pair and after the exposure ends read out said target in the progressive scan mode and store the digital pixel data for the resulting image frame in another memory, make a selected one of a low energy or a high energy post-contrast exposures in a pair and read out said target in the progressive scan mode while concurrently combining by subtraction the digital pixel data for this image frame with the corresponding stored digital pixel data for said pre-contrast image made at the same energy and store the resulting difference image data in a third memory, read out the third memory and store the difference image data in a mass storage device as one of the temporal difference images obtained with the same high or low X-ray energy, make the other of the low energy or high energy post-contrast exposures in the pair and read out said target in the progressive scan mode while concurrently combining by subtraction the digital data for this image frame with the corresponding stored digital data for said pre-contrast image made at the same energy and store the resulting difference image data in said third memory as the other of the temporal difference images obtained with the same but other of the high or low X-ray energies, and read out said third memory again and store the data in said mass storage device as the other of the temporal difference images obtained with the same low or high X-ray energy, such that there is data representative of at least one low energy temporal difference image and data representative of at least one high energy temporal difference image in storage, and including the steps for hybrid subtraction to effect cancellation of any soft tissue motion artifacts present in temporal difference images, comprising:

retrieving from storage a frame of pixel data representative of a low energy temporal difference image and multiplying said data by a coefficient, $k_l$, retrieving from storage a frame of pixel data representative of a high energy temporal difference image and multiplying said data by a coefficient, $k_h$, after said multiplications, finally subtracting the data for one of the low energy and high energy temporal difference images from the other to yield a final difference image frame of pixel data and using this data to drive a television means for displaying the final image, the values of $K_l$ and $k_h$ being chosen such that the final subtraction will result in soft tissue motion artifacts being cancelled and the contrast medium defined region remaining.

8. The method according to claim 7 including the steps for optimizing soft tissue artifact cancellation, wherein, after said final image is displayed, one or the other or both of the selected low energy temporal difference image data and the selected high energy temporal difference image data are multiplied by a coefficient having a different value from the value first used and the final image is displayed for determining if soft tissue artifact cancellation has been improved.

9. A method of producing a visible image of a body region defined by the X-ray contrast medium it contains wherein:

pre-contrast X-ray exposures are made before the medium enters the region and post-contrast exposures are made after it eners; pairs of exposures are made in succession with low and high average energy X-ray beams in either order; an image resulting from an exposure is formed on the target of a television camera; and, analog video signals resulting from scan readout of said target are converted to digital logarithmic data representative of picture elements (pixels) composing a frame; said method including the following steps:

make a selected one of a low energy or a high energy pre-contrast X-ray exposures in a pair and after the exposure ends read out said target in the progressive scan mode and store the digital pixel data for the resulting image frame in one memory and after readout is complete make the other of said exposures in the pair and after the exposure ends read out said target in the progressive scan mode and store the digital pixel data for the resulting image frame in another memory, make a selected one of a low energy or a high energy post-contrast exposures in a pair and read out said target in the progressive scan mode while concurrently combining by subtraction the digital pixel data for this image frame with the corresponding stored digital pixel data for said pre-contrast image made at the same energy and store the resulting difference image data in a third memory, read out the third memory in the interlaced mode and convert this digital data to analog video signals and store the difference image data in analog form in a mass storage device as one of the temporal difference images obtained with the same high or a low X-ray energy, make the other of the low energy or high energy post-contrast exposures in the pair and read out said target in the progressive scan mode while concurrently combining by subtraction the digital data for this image frame with the corresponding stored digital data for said pre-contrast image made at the same energy and store the resulting difference image data in said third memory as the other of the temporal difference images obtained with the same but other of the high or low X-ray energies, and read out said third memory again in the interlaced mode and convert this digital data to analog video signals in analog form in said mass storage device as the other of the temporal difference images obtained with the same low or high X-ray energy, such that there is data representative of at least one low energy temporal difference image and data representative of at least one high energy temporal difference image in storage, including the steps for hybrid subtraction to effect cancellation of any soft tissue motion artifacts present in temporal difference images, comprising:

reading from mass storage analog video signals representative of a low energy temporal difference image frame, converting said signals to digital pixel data and storing the data in a memory, reading from mass storage analog video signals representative of a high energy temporal difference image frame, converting said signals to digital pixel data and storing this data in another memory, transferring low energy temporal difference image digital data and the high energy temporal difference image data from the respective memories to a processor and causing the processor to multiply the low energy pixel data by a coefficient, $k_l$, and the high energy pixel data by a coefficient, $k_h$, and subtract pixels of one frame of image data from corresponding pixels in the other to yield a final difference image frame of pixel data, and then using the final data to drive television means for displaying the final image, the values of $k_l$ and $k_h$ being chosen such that the final subtraction will result in soft tissue motion artifacts being cancelled and the contrast medium defined region remaining.

10. The method according to claim 9 including the steps for optimizing soft tissue artifact cancellation wherein, after said final image is displayed, one or the other or both of the selected low energy temporal difference image data and the selected high energy temporal difference image data are multiplied by a coefficient have a different value from the value first used and the final image is displayed for determining if soft tissue artifact cancellation has been improved.

11. A method of producing a visible image of a body region defined by the X-ray contrast medium it contains wherein:

pre-contrast X-ray exposures are made before the medium enters the region and post-contrast exposures are made after it enters; pairs of exposures are made in succession with low and high average energy X-ray beams in either order; an image frame resulting from an exposure is formed on the target of a television camera; and, analog video signals resulting from scan readout of said target are converted to digital logarithmic data representative of picture elements (pixels) composing a frame; said method including the following steps:

make a low X-ray energy pre-contrast exposure and during a following frame time read out said target in the progressive scan mode and store the digital pixel data for the image frame in a first memory as the low energy pre-contrast mask image, either before or after making said low energy pre-contrast exposure, make a high energy pre-contrast exposure a short time after target readout of the preceding exposure is complete and during a following frame time read out said target in the progressive scan mode and store the digital pixel data for the image frame in a second memory as the high energy pre-contrast mask image, make a low energy live post-contrast exposure and during a following frame time read out said target in the progressive scan mode and during readout subtract the live low energy post-contrast digital pixel data from corresponding low energy pre-contrast pixel data that is stored in the first memory and store the results in progressive scan format in a third memory as the low energy temporal difference image data in which substantially everything that is common to the two images is subtracted out except soft tissue motion artifacts, if any, and substantially only the region defined by contrast medium remains, either before or after making said low energy post-contrast exposure make a live high energy post-contrast exposure and during the time of this exposure read out in the interlaced scan mode the low energy temporal difference image from said third memory and store the same in mass storage, and during a frame time following the high energy post-contrast read out said target in the progressive mode and while the resulting digital pixel data are being produced subtract the same from corresponding digital pixel data of the high energy pre-contrast image that is stored in said second memory and store the results in a fourth memory in progressive format as the high energy temporal difference image wherein substantially everything that is common to the two images is subtracted out except for soft tissue motion artifacts, if any, and substantially only the region defined by the contrast medium remains, read out the low energy temporal difference image data from said third memory in the interlaced scan mode to processor means while simultaneously reading out the high energy temporal difference image data from said fourth memory in the interlaced scan mode to said processor means and with said processor means multiply the low energy image data by a coefficient, $k_l$, and multiply the high energy image data by a coefficient, $k_h$, to produce two data sets that are modified for soft tissue cancellation, after said multiplication steps subtract one of said sets from the other and store the resulting data in mass storage as a hybrid subtraction image.

12. The method according to claim 11 including the steps for obtaining additional hybrid subtraction images wherein:

said low energy pre-contrast image data are retained in said first memory and said high energy pre-contrast image data are retained in said second memory after one hybrid subtraction image is stored in mass storage, then repeating the steps in claim 11 which follow the first two steps of obtaining and storing a low energy pre-contrast mask image in the said first memory and a high energy pre-contrast mask image in said second memory, to thereby obtain additional hybrid subtraction images for storage in said mass storage.

13. The method according to any of claims 11 or 12 wherein:

while said low energy temporal difference image data is being read out in interlaced format and stored in mass storage, said data are used concurrently to effect display of the low energy temporal difference image on a television screen.

14. The method according to any one of claims 11 or 12 wherein after the image on said target resulting from an exposure at one energy is read out, said target is scrubbed for at least one television frame before an exposure at the other X-ray energy is made.

15. Apparatus for producing a visible image of a body region defined by the X-ray contrast medium it contains including an X-ray source, means for controlling said source to expose a body region before (pre-contrast) and after (post-contrast) an X-ray contrast medium enters said region to a low average energy X-ray beam or alternately to a high average energy beam when low kilovoltage (kV) and high kV, respectively, are applied to the X-ray source, television camera means having an image target whose scan readout results in converting X-ray image frames resulting from said exposures to analog video signals, means for converting said signals to digital data corresponding in value to the intensities of the picture elements (pixels) that compose a frame, and means for converting digital values to logarithmic equivalents:
- first memory means for storing the pixel data for a mask image resulting from a high energy pre-contrast exposure,
- second memory means for storing the pixel data for a mask image resulting from a high energy pre-contrast exposure made shortly after said low energy pre-contrast exposure,
- third memory means,
- video signal recording means, and means for transferring means to said recording means video signals corresponding to digital pixel values for images stored in said third memory means,
- processor means operating sequentially to subtract live image pixel data resulting from a low energy post-contrast exposure from corresponding pre-contrast low energy exposure image data that is stored in said first memory means and providing the results of said subtraction to said third memory means whereupon said transferring means will transfer said results to said recording means as the low energy temporal difference image and operating to subtract the next occurring live image pixel data resulting from a high energy post-contrast exposure from corresponding pre-contrast high energy exposure image data that is stored in said second memory means and providing the results of said subtraction to said third memory means whereupon said transferring means will transfer said results to the recording means as the high energy temporal difference image, television display means, and
- means for supplying data from said recording means representative of a low energy and a high energy temporal difference image simultaneously to said processor means for said processor means to multiply the low energy temporal difference image data by a coefficient, $k_l$, and the high energy temporal difference image data by a coefficient, $k_h$, and to subtract the resulting data for one image from that of the other to thereby produce a hybrid subtraction image data set for display by said television display means.

16. Apparatus for producing a visible image of a body region defined by the X-ray source, means for controlling said source to expose a body region before (pre-contrast) and after (post-contrast) an X-ray contrast medium enters said region to a low average energy X-ray beam or alternately to a high average energy beam when low kilovoltage (kV) and high kV, respectively, are applied to the X-ray source, television camera means having an image target whose scan readout results in converting X-ray image frames resulting from said exposures to analog video signals, means for converting said signals to digital data corresponding in value to the intensities of the picture elements (pixels) that compose a frame, and means for converting digital values to logarithmic equivalents:
- first memory means for storing the pixel data for a mask image resulting from a low energy pre-contrast exposure,
- second memory means for storing the pixel data for a mask image resulting from a high energy pre-contrast exposure made shortly after said low energy pre-contrast exposure,
- processor means,
- third memory means for storing difference image digital pixel data resulting from subtraction by said processor means of the low energy mask image data in said first memory means and the live image data resulting from a low energy post-contrast exposure,
- fourth memory means for storing difference image digital pixel data resulting from subtraction by said processor means of the high energy pre-contrast image data in the second memory means and the live image data resulting for a high energy post-contrast exposure,
- said processor means operating to multiply simultaneously the difference image pixel data from said third memory means and difference image pixel data from said fourth memory means by coefficients $k_l$ and $k_h$, respectively, and said means subtracting one of the sets of data resulting from said multiplications from the other to produce a digital image data set representative of a hybrid subtraction image,
- means for converting said last named digital data set to analog video signals, and means for storing the video signals.

* * * * *

UNITED STATES PATENT AND TRADEMARK OFFICE
CERTIFICATE OF CORRECTION

PATENT NO. : 4,482,918

DATED : November 13, 1984

INVENTOR(S) : Gary S. Keyes, Stephen J. Riederer,
Thomas W. Lambert and Barry N. Stone It is certified that error appears in the above-identified patent and that said Letters Patent are hereby corrected as shown below:

Column 18, line 31, after "elements" insert ---pixels---.

Column 20, line 40, delete "said" (second occurrence).

Column 22, line 3, change ---eners--- to ---enters---.

Column 25, line 4, change "high" to ---low---.

Signed and Sealed this

Eighth Day of October 1985

[SEAL]

Attest:

DONALD J. QUIGG

Attesting Officer

Commissioner of Patents and Trademarks—Designate